United States Patent [19]

Schenck et al.

[11] Patent Number: 4,624,255

[45] Date of Patent: Nov. 25, 1986

[54] APPARATUS FOR ANASTOMOSING LIVING VESSELS

[76] Inventors: Robert R. Schenck, 1100 N. Lake Shore Dr., Chicago, Ill. 60611; Harry P. Weinrib, 2644 W. Estes Ave., Chicago, Ill. 60645

[21] Appl. No.: 734,389

[22] Filed: May 14, 1985

Related U.S. Application Data

[63] Continuation of Ser. No. 548,867, Sep. 29, 1983, abandoned, which is a continuation of Ser. No. 349,885, Feb. 18, 1982, Pat. No. 4,474,181.

[51] Int. Cl.[4] .............................................. A61B 17/11
[52] U.S. Cl. ................................. 128/334 R; 128/346
[58] Field of Search ............... 128/334 C, 334 R, 335, 128/346, 326, 340

[56] References Cited

U.S. PATENT DOCUMENTS

| | | | |
|---|---|---|---|
| 3,221,746 | 12/1965 | Noble | 128/334 R |
| 3,254,650 | 6/1966 | Collito | 128/334 C |
| 3,254,651 | 6/1966 | Collito | 128/334 C |
| 3,538,917 | 11/1970 | Selker | 128/326 |
| 4,165,747 | 8/1979 | Bermant | 128/334 C |
| 4,366,819 | 1/1983 | Kaster | 128/334 C |

FOREIGN PATENT DOCUMENTS

395074  1/1974  U.S.S.R. ........................... 128/334 C

OTHER PUBLICATIONS

D. A. Donetskii, "A New Method for a Circular Vascular Suture", (1956 Eksperim Khirur. 1.), pp. 53–59.

Primary Examiner—Michael H. Thaler
Attorney, Agent, or Firm—Fitch, Even, Tabin & Flannery

[57] ABSTRACT

To effect a simple anastomosis of a pair of severed blood vessel portions in a manner which insures patency of the anastomozed blood vessel, a member, preferably in the form of a ring, has structure for tethering the blood vessel portions thereto under radial stress with the intima of the blood vessel portions apposed. During surgery, the ring is disposed around an end of one of the severed blood vessel portions, and the blood vessel portions are tethered to the ring at at least three spaced apart locations stressing the blood vessel portions radially outward in several directions to evert the intima and hold the intima of the two portions against each other.

To hold blood vessel portions in close proximity during anastomosis, a pneumatic clamping device is provided which grips the blood vessel portions with a precise force according to the fluid pressure supplied thereto. Precise control of gripping force assures a firm grip that is not excessive and does not damage the blood vessel portions. Preferably a portion of the clamping device is integrally formed with the ring and is frangible therefrom permitting the clamping device and ring to be prepackaged in a sterile container with the ring prepositioned relative to the clamping device and separated upon completion of the anastomosis.

12 Claims, 23 Drawing Figures

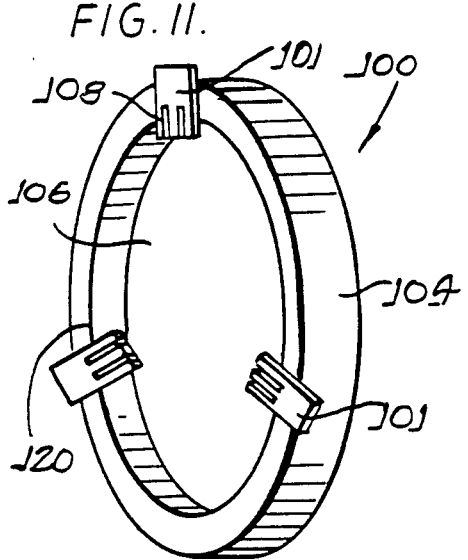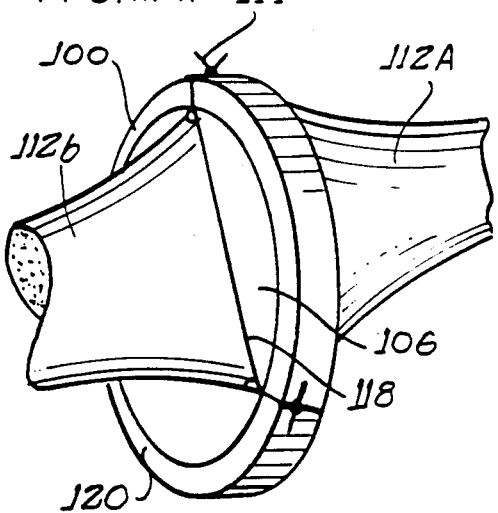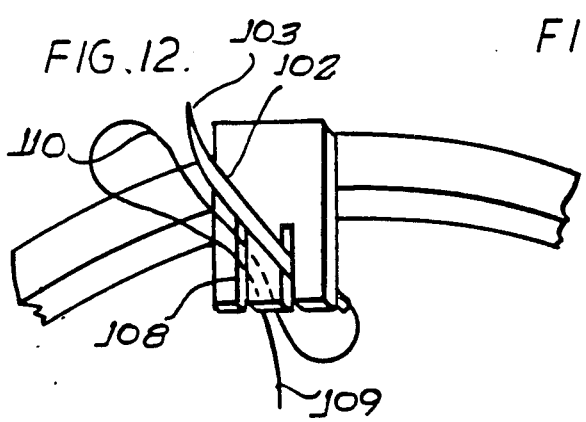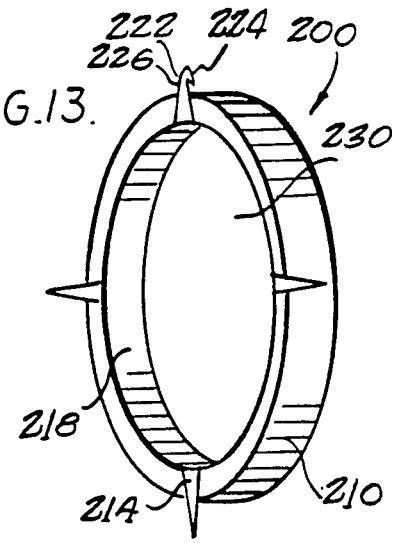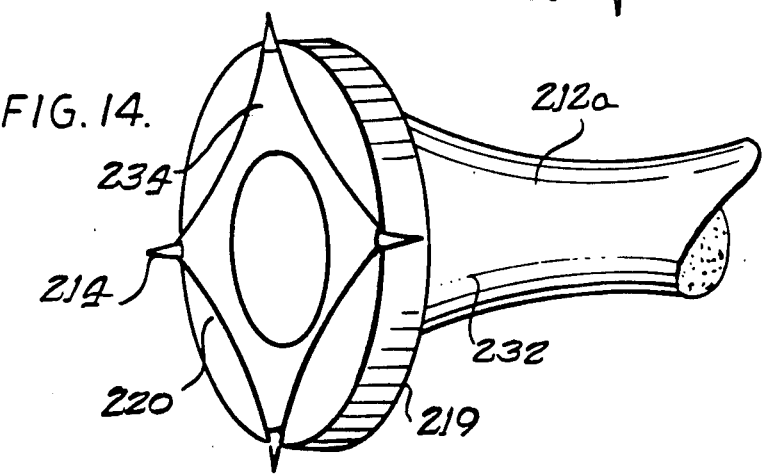

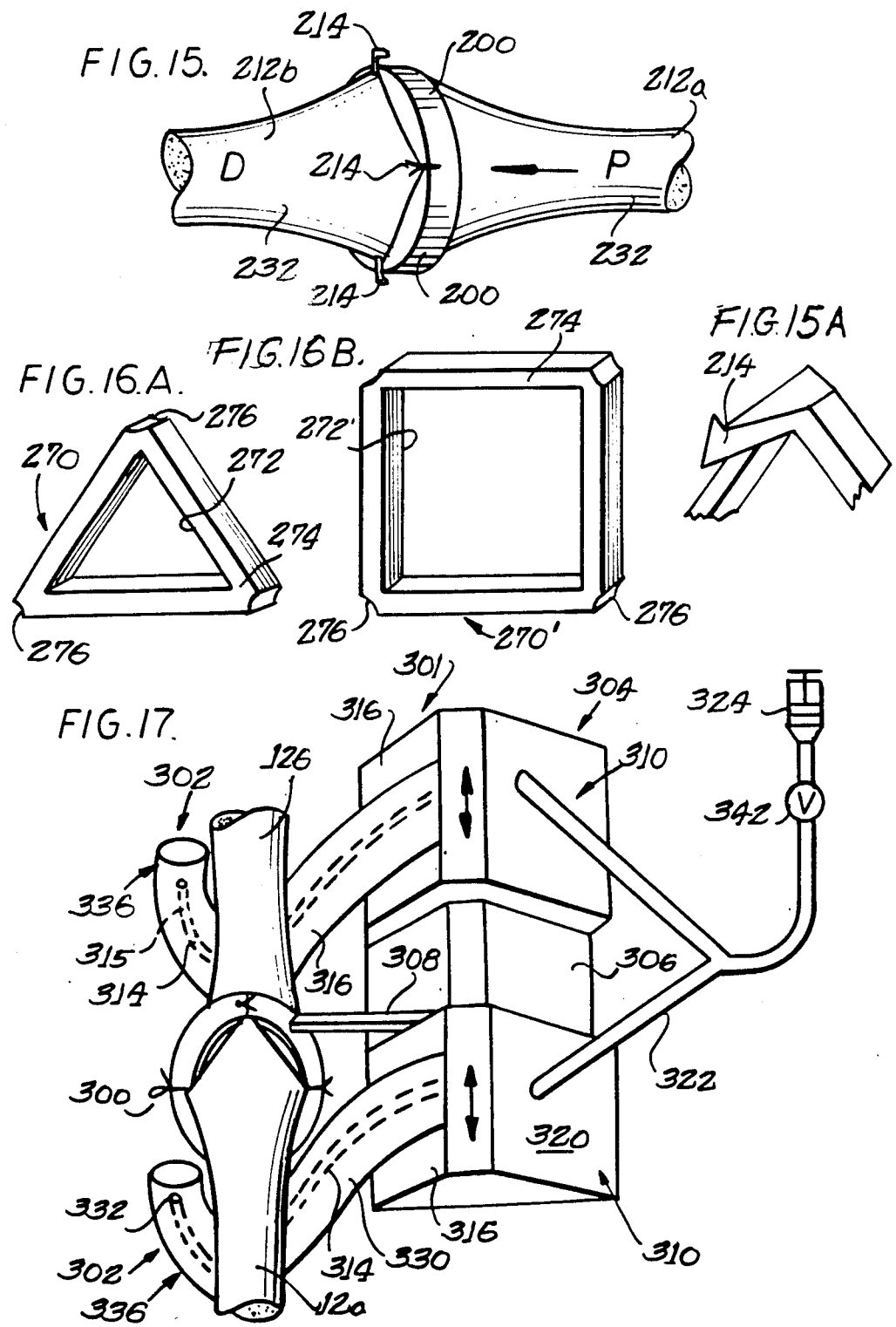

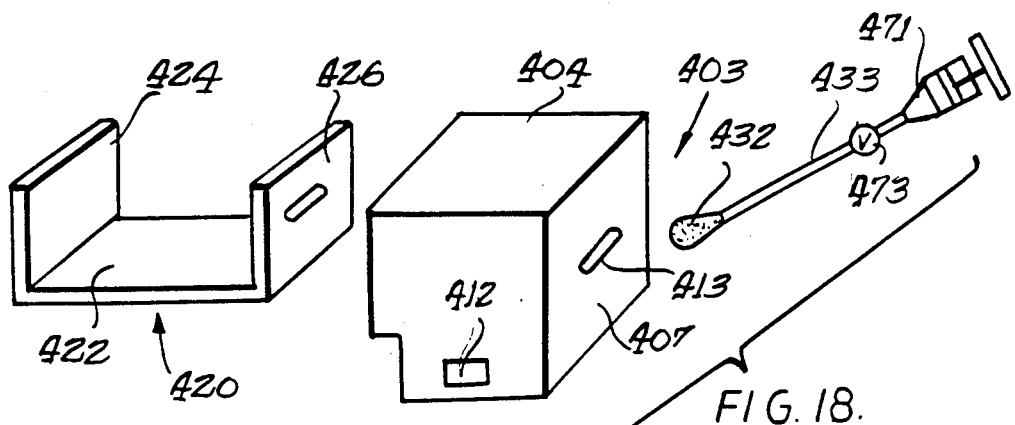
FIG. 18.
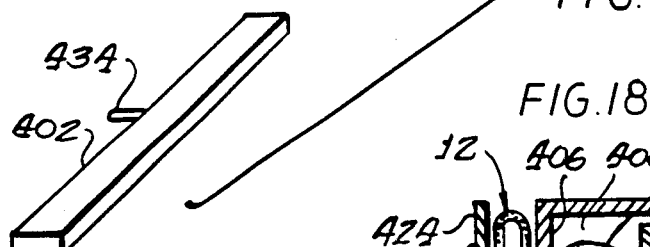
FIG. 18A.
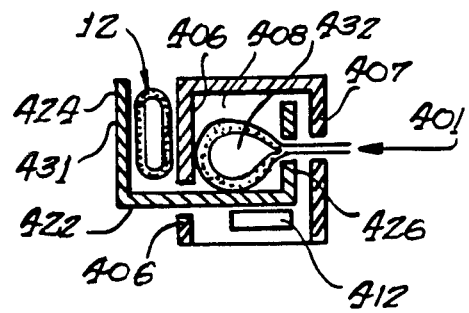
FIG. 19.
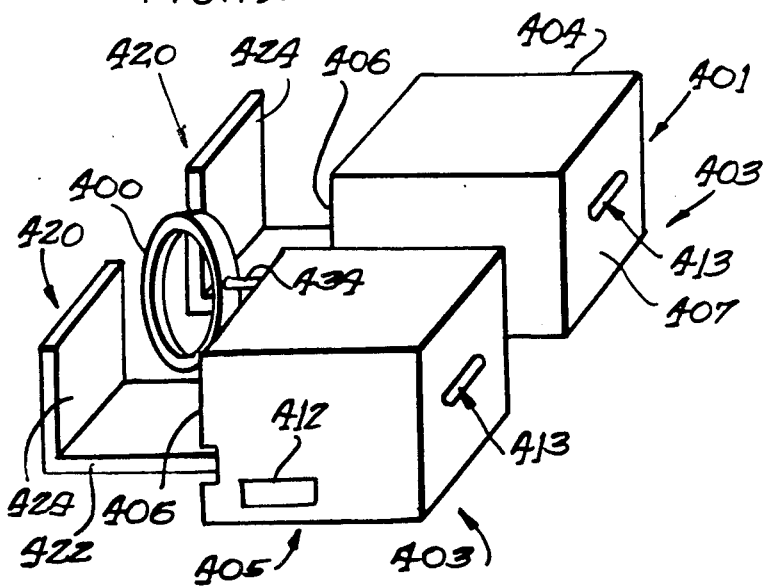

APPARATUS FOR ANASTOMOSING LIVING VESSELS

This is a continuation of patent application Ser. No. 548,867 filed Sept. 29, 1983, abandoned, which is a continuation in part of Ser. No. 349,885, filed Feb. 18, 1982 now Pat. No. 4,474,181. The present invention relates to methods and apparatus for joining severed ends of blood vessels.

Among the important and time consuming tasks in surgical procedures is the anastomosis or joining of severed blood vessels, and the success of a surgical procedure may depend on the degree of circulation which is restored through such anastomosis. Anastomosing of blood vessels is a tedious procedure, particularly in blood vessels of small diameter including blood vessels less than one mm. in diameter. Conventional blood vessel suturing techniques are time consuming, extending the duration of a surgical procedure and successful anastomosing of blood vessels is highly dependent on the proper placement of sutures by the surgeon. Particular difficulty is often encountered in anastomosing children's vessels which are small and prone to spasm.

To aid in anastomosing blood vessels, implantable devices which connect severed ends of blood vessels have been described previously, e.g., U.S. Pat. Nos. 3,254,650 and 4,055,186, British Patent Specification No. 1,181,563, German Fed. Rep. Pat. No. 2,101,282 and Nakayama et al. Surgery December 1962, pp. 918-931. Devices have also been described for everting severed ends of blood vessels to facilitate their suturing, e.g., U.S. Pat. No. 2,180,337. The need continues for improved methods and apparatus for anastomosing blood vessels, particularly tiny blood vessels.

Blood vessels of all but the largest size, i.e., the aorta and vena cava in humans, have a naturally occuring contractility, identified as circumferential compressive stress, that resists dilation. These forces become proportionately larger as the vessel diameter decreases and the relative wall thickness increases. Radial tethering forces of tissues do exist around the vessel, but these are of lesser significance than longitudinal vessel motion tethering.

Successful suturing of blood vessels does not assure their continued patency, i.e., their ability to conduct blood flow. Thrombosis (clotting of blood) may act to block blood flow through an anastomosed vessel. In addition to inaccurate placement of sutures, several other factors—spasm, stenosis, and microclamp damage—may be additive in causing thrombosis after microvasuclar repair. It has been found that continuity of flow during the first twenty minutes after anastomosis is critical in preventing thrombus formation. It has also been found that platelet aggregation, and later resolution occurs in the first several hours after a microvascular anastomosis.

It is a general object of the present invention to provide methods and apparatus which simplify surgical anastomosis techniques and which effect an anastomosis with substantial assurance of patency.

Herein, an external ring is provided which is placed around one end of a blood vessel portion to be joined. Means, such as sutures or hooks, are provided to radially tether the blood vessel portions to the ring at various circumferal locations to apply outward radial stress to the portions. The tethering holds the intima of the severed ends together forming a fluid-tight seal and promoting healing while minimizing both the number and exposure of the sutures, thereby reducing the likelihood of significant thrombosis occurring at the anostomosis site. The outward radial stress maintains an open blood flow passageway at the junction during healing.

Anastomosis of severed blood vessel portions requires that the severed portions be held in close proximity to permit the surgeon to perform the necessary joining operation. A frequently used type of clamp for this purpose consists of a pair of spring clamps mounted at spaced apart intervals along a bar, each clamp pinching one of the severed blood vessel portions to hold them in place for anastomosis. The force with which the clamps grip the blood vessel must be sufficient to hold them in place, and generally the clamp must exert about 15 gm. pressure. On the other hand, excessive pressure of the metal clamps will damage the blood vessel portions and it is considered very undesirable that a clamp exert over about 35 gm. pressure to the blood vessel. Thus the clamp should grip the blood vessel portions applying pressure within a very narrow range that is difficult to achieve with conventional microclamps.

It is another general object of the invention to provide clamping devices whose gripping force can be precisely adjusted to grip the blood vessel with a predetermined amount of force and with less damage to the blood vessel.

The clamping device comes into intimate contact with the internal regions of the body and must be presterilized. During surgery the anastomosis device must be positioned relative to the clamping device. Time could be saved during surgery if the anastomosis device were prepositioned relative to the clamping device.

It is another general object of the invention to provide an anastomosis device which is attached to a clamping device prepositioned therein and easily removable from the clamping device after surgery so that the clamping device can be disposed of.

These and other objectives and advantages of the invention will become more apparent from the following detailed description of the invention in reference to the accompanying drawings in which:

FIG. 11 is a perspective view of a further alternative embodiment of an anastpmosis ring having preattached sutures and surgical needles;

FIG. 11A is a perspective view of the anastomosis ring of FIG. 11 with a pair of blood vessel portions sutured thereto;

FIG. 12 is a perspective view of the suture and surgical needles of FIG. 11;

FIG. 13 is a perspective view of a still further embodiment of an anastomosis ring;

FIG. 14 is a perspective view of the suture ring of FIG. 13 having one blood vessel end portion tethered thereto;

FIG. 15 is a perspective view of the suture ring of FIG. 13 having two blood vessel end portions tethered thereto;

FIG. 16A is a further alternative embodiment of an anastomosis device having a triangular configuration;

FIG. 16B is a further alternative embodiment of an anastomosis device having a square configuration;

FIG. 17 is a perspective view of an anastomosis ring attached to a pneumatic or hydraulic clamping device embodying various features of the present invention, a pair of blood vessel portions shown clamped thereto;

FIG. 18 is an exploded perspective view of parts of an alternative embodiment of a pneumatic or hydraulic clamping device shown in FIG. 19;

FIG. 18a is a reduced size cross-sectional view taken through the device of FIG. 19.

FIG. 19 is a perspective view of another embodiment of the invention.

Figure 1:
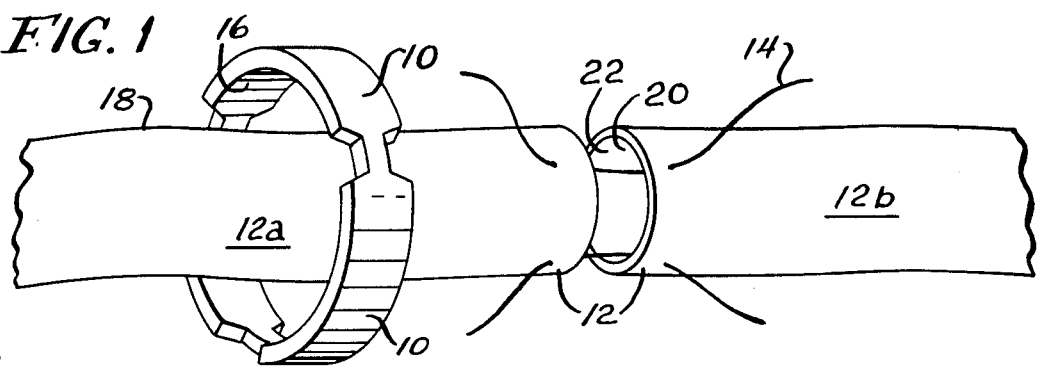
FIG. 1 is a perspective view of an anastomosis ring, embodying various features of the invention, disposed around a severed end of a blood vessel portion and sutures threaded through two blood vessel end portions to be anastomosed.

In accordance with the present invention, severed blood vessel portions are reconnected with outward radial stress applied to the blood vessel at the anastomosis site to keep blood flow passageways dilated and otherwise maintain patency of the connected blood vessel portions. The portions are anastomosed by placing an external (to the blood vessel) member 10 around an end 12a of one of the severed blood vessel portions 12, tethering the portions 12a, b, at three or more locations with means such as sutures 14 or hooks 214 (FIG. 13) to radially outwardly stress the vessel portions everting their intima and holding their intima in fluid-tight apposition. (It is to be understood that the blood vessel portions need not originally be portions of the same blood vessel).

The member 10, illustrated in FIG. 1, is in the form of an annular ring formed of material which is biocompatible for implantation in a living body of an animal, such as a human. The ring 10 has means 19, such as grooves or notches, at spaced-apart locations for tethering sutures 14. The tethering of the connected blood vessel 12 not only holds the blood flow passageway 20 open but dilates the blood vessel portions at the anastomosis site enlarging the blood flow passageway, thereby reducing the chance of thrombosis occurring and clogging the passageway. The stretching also serves to evert the interior surfaces or intima 22 of the blood vessel tightly apposing the intima to aid prompt healing.

The annular shape of the ring 10 corresponds to the generally circular cross section of blood vessels 12. In order to provide for stretching of the connected blood vessel end portions 12a, 12b toward the ring, the interior surface 16 of the ring has an inside diameter at least 25 percent longer than the outside diameter of the blood vessel which the ring is adapted to surround, and preferably the inside diameter of the ring is between 50 percent and 200 percent larger than the diameter of the blood vessel. Although there is no inherent upper limit on ring size as compared to the size of the blood vessel for anastomosis purposes, the ring, being a foreign object within the body, is preferably as small as possible consistent with suture attachment providing radial tethering stress. The ring need be no longer or no thicker than is consistent with its structural integrity.

External anastomosis rings 10 may be formed of any material of sufficient strength to support the tethered blood vessels and is biocompatible or can be made biocompatible with an appropriate coating. Suitable biocompatible materials include but are not limited to stainless steel, graphite, pyrolytic carbon, tungsten, tantalum and polymeric material, such as polytetrafluorethylene. In a preferred embodiment, the ring 10 is formed or a material, which is not only biocompatible but is dissolved or otherwise degraded after a period of time by the body of the animal. Suitable biocompatible materials for rings which are dissolved or degraded after a healing period include collagen, polyglycolic acid, polylactic acid and combinations of polyglycolic and polylactic acid.

The attachment means 19 provided at spaced-apart locations on the ring 10 facilitate tethering of the sutures 14 to the ring and maintain the positioning of suture ties 26 (FIG. 3) around the ring. At least three such attachment means 19 are provided for tethering the connected blood vessel ends 12a,b at three locations and so insure an open passageway 20 in the connected, tethered blood vessel. The attachment means 19 are preferably evenly spaced, an arrangement which maximizes the passageway size for the number of sutures used, for example, if three attachment means are used, they are disposed about 120° apart around the ring. Increasing the number of attachment means 19, to which are tethered a corresponding number of sutures, tends to enlarge the passageway 20 at the anastomosis site while permitting the use of a smaller tethering ring; however, each additional suture increases the time needed for anastomosis, and accordingly, it is preferred for smaller blood vessels, that only three attachment means 19 be provided for tethering three sutures 14. However, for larger blood vessels, a ring having up to six or more attachment means might be provided.

In the embodiment illustrated in FIG. 1, notches 19 in the ring 10 provide the means for attaching and positioning the sutures 14 during tethering. Three pairs of notches 19 are illustrated, the notches of each pair being formed in opposite ends of the ring 10. Notches 19 are simply formed and conveniently utilized during surgery, requiring no threading or other tedious and time consuming techniques. The surgeon need not tether the sutures 14 initially in the notches 19 but may shift loosely tethered sutures into the notches after the ties 26 have been initially knotted around unnotched portions of the ring 10.

Figure 2:
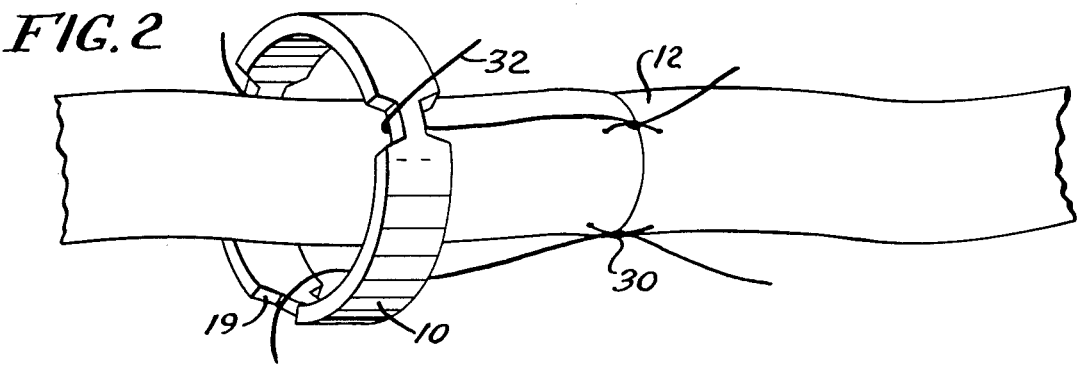
FIG. 2 is a perspective view of an anastomosis ring of FIG. 1 showing the sutures tied to connect the blood vessel end portions by sutures.
Figure 4:
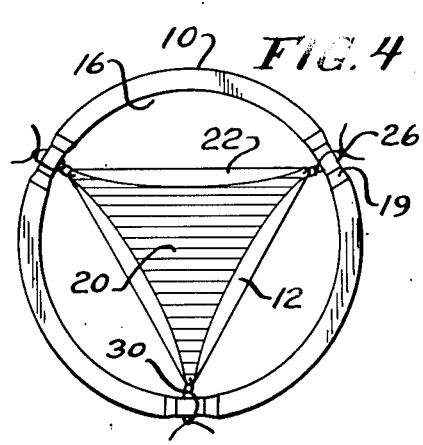
FIG. 4 is a plan view showing one of the two severed ends sutured and tethered to the ring.

To end-to-end anastomose a blood vessel 12, the end portions of the blood vessel are prepared for suturing in a medically acceptable manner, and the ring 10 is placed around one of the severed ends 12a as seen in FIG. 1. The sutures 14, corresponding in number to the notches 19, are then threaded through the walls of the blood vessel portions at spaced apart locations (FIG. 1), each suture being threaded through both of the severed end portions 12a,b in adjacent circumferential locations. The threaded sutures are then tied into a knot 30 (FIG. 2) connecting the severed end portions 12a,b of the blood vessel and leaving a free end 32 of each suture with sufficient length for tethering to the surrounding ring 10. Thereafter, the free ends 32 of the sutures 14 are looped around the ring 10, drawn outward to pull the blood vessel end portions radially outward toward the ring and tied into knots 26 located within the notches 19. The tethered sutures 14 stretch the blood vessel end portions 12a,b providing a polygonal blood passageway, e.g., where three sutures are used, the passageway is generally triangular as best seen in FIG. 4. Because the walls of the blood vessel portions 12a,b are stretched, the blood vessel end portions are dilated, and the polygonal opening provides a blood flow passageway 20 which is typically as large or larger than the natural circular passageway of the blood vessel.

The stretching of the blood vessel portions by the tethering sutures 14 also everts the intima 22 of the blood vessel end portions 12a, 12b and hold them in tight apposition to each other, as seen in FIG. 4, so that a fluid-tight seal is formed therebetween, and flowing blood primarily contacts the intima of the connected blood vessel end portions. Fewer sutures 14 are used than are generally used in conventional anastomosis techniques, and the tenting effect achieved by tethering minimizes the exposure of the sutures 14 to flowing blood, thereby reducing suture-induced thrombosis.

Figure 7:
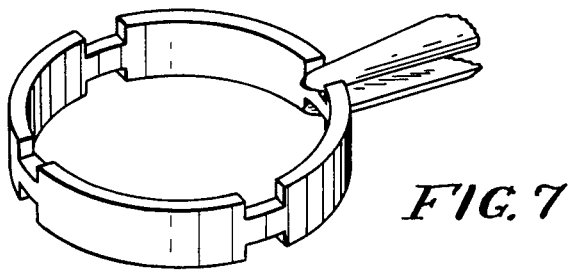
FIG. 7 is a perspective view of an alternative embodiment of an anastomosis ring having means for tethering four blood vessel-connecting sutures.
Figure 8:
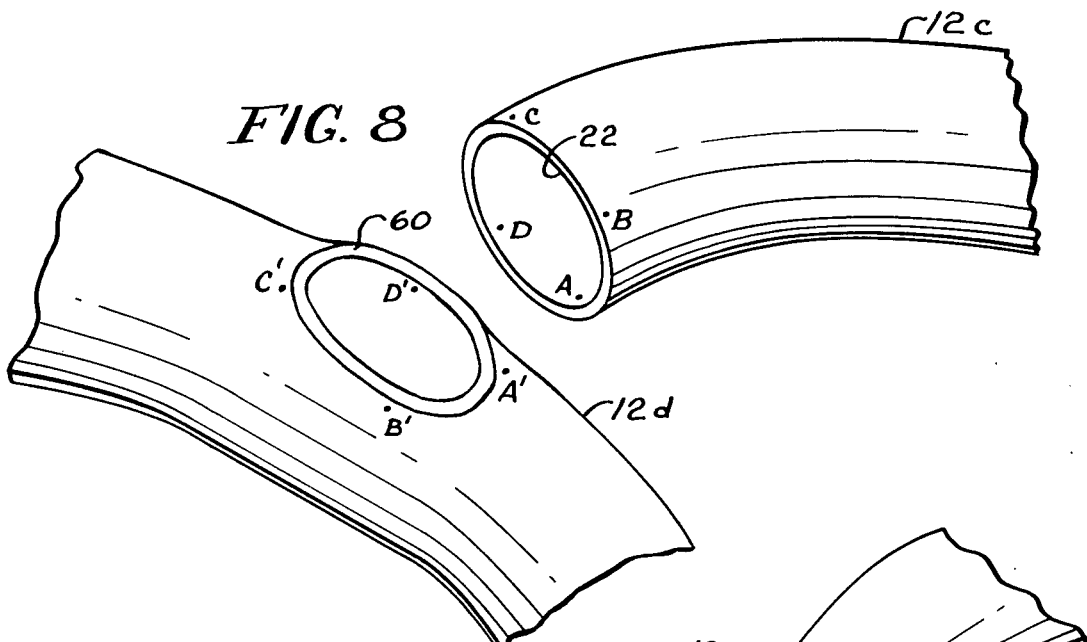
FIG. 8 is a perspective view of an end of one blood vessel prepared for anastomosis to a prepared side of another blood vessel.
Figure 9:
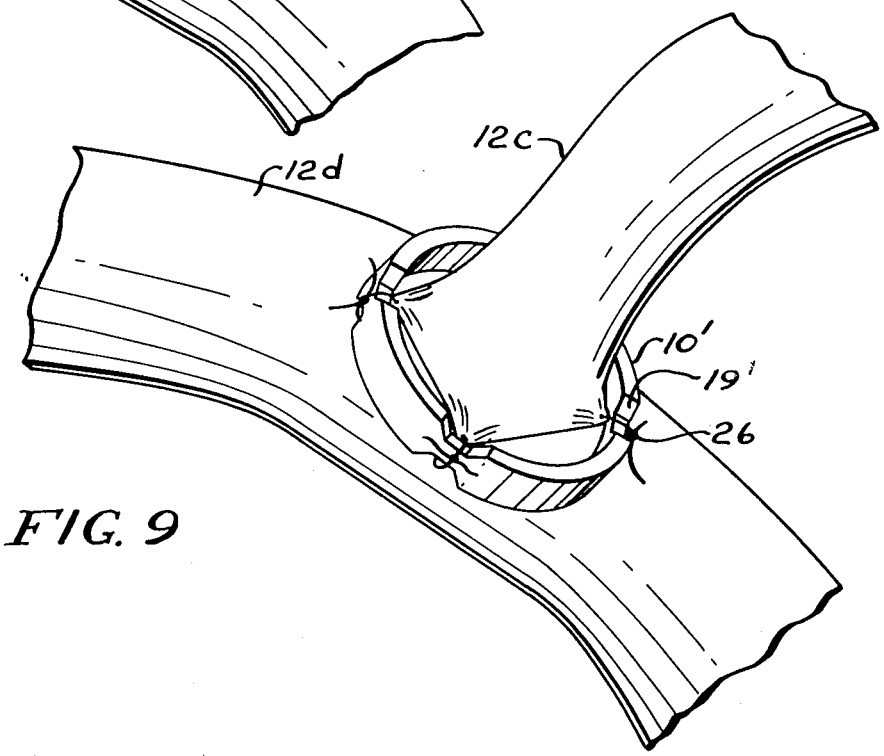
FIG. 9 is a perspective view of the end-to-side anastomosis performed with the ring of FIG. 7 on the prepared blood vessel of FIG. 8.

Illustrated in FIGS. 7-9 is an end-to-side anastomosis, such as may be used to form a shunt between one blood vessel portion and another. The illustrated anastomosis uses an anastomosis ring 10' having four notch pairs 19' spaced 90° from each other for attaching four tethering sutures 14. In this case, a prepared end portion 12c of one blood vessel is connected to another blood vessel portion 12d which has been prepared for anastomosis by cutting a generally circular opening 60, substantially the same size as the passageway 22, through side wall of the blood vessel end portion 12c. The interior diameter of the ring 10' is significantly larger than the exterior diameter of the blood vessel end portion 12c so that when the blood vessel portions 12c,d are joined, the ring is spaced radially outward from the anastomosis site, whereby the tethering sutures 14 apply outward radial stress to the connected portions.

Four discontinuous sutures are used to connect the prepared portions 12c,d (FIG. 8) by threading them through locations, indicated at A, B, C, and D, generally evenly spaced around the circumference of the end portion 12c and corresponding locations A', B', C', and D', generally evenly spaced around the opening 60. The sutures 14 are tied to connect the vessel portions 12c,d and then tethered to the four pairs of notches 19' to form the generally square anastomosis illustrated in FIG. 9.

Further convenience for the surgeon permitting faster surgery is provided by pre-attaching sutures 101 and needles 102 to an anastomosis ring 100 as illustrated in the embodiment shown in FIG. 11. The ring 100 is a section of a tube formed of a bioabsorbable or biodegradable material, such as polyglycolic acid, has an exterior surface 104 and an interior opening 106. The exterior and interior surfaces may be circular, as in FIG. 11, or they may be triangular, as shown in FIG. 16A, or they may be rectangular or square as shown in FIG. 16B. At the corners of the interior opening 106, a suture holder 101 is fastened with an adherent. The holder is a small sheet of paper or light plastic with two slits 108 to keep needles 102 (FIG. 12) with a preformed loop of suture 110. Needles 102 will be used just for one stitch and disposed so it can be made from the hard plastic or steel. When the needle end 103 has been inserted and passed through the two vessel walls, it is then projected into and passed through the preformed loop 110, and when traction on the needle end and the tail 109 is given, a knot is automatically formed under the ring. The two ends are then tied around the ring in the usual fashion.

The ring 100 with four threaded sutures is packaged as a unit in a sterile manner. During surgery, the physician merely had to place the ring 100 around one severed blood vessel end portion 112a and then pierce each needle end 103 through adjacent locations of two blood vessel portions 112a, 112b, extend each needle through the suture loop 110 and tie a surgical knot using the preformed loop. After the knot 114 is tied, the free ends of the suture 101 are cut to remove the needles 102, which are disposed of, and the holders 101 also may be detached and disposed of.

Three or four knots are used to tether the joined blood vessel portions 112 under radial tension to the corners of the square or triangular interior opening 106 holding the intima of the blood vessel portions 112 in fluid tight apposition to each other. Between the corners of the opening 106, the edges 118 of the dilated, joined blood vessel portions 112 are stretched to extend closely adjacent the side edges 120 whereby the ring 100 and blood vessel portions mutually support each other in axial alignment helping to maintain patency of the blood vessel during healing.

Illustrated in FIGS. 13-15 is an embodiment of a suture ring 200 in which severed blood vessel portions 212a, 212b are intimately apposed through radial tethering without the use of sutures. Instead, the blood vessel portions are tethered to the ring 200 by means of hooks 214 integrally formed with the ring and disposed at evenly spaced locations at points along a circle of greater diameter than the diameter of the blood vessel portions 212. The illustrated ring 200 has a circular exterior 210, a circular interior 218 and flat end faces 219, 220. The hooks 214 are formed as protuberances raised from one end face 220 and have portions 222 that extend outward beyond the ring exterior 216. Each outwardly extending portion 222 has a doubled backed segment 224 with a pointed end 226 for puncturing the blood vessel portions 212. Doubling the end segment 224 back so that the point 226 extends inward toward the body of the ring 200 forms a fish hook to hold the blood vessel portions against removal and minimizes irritation of the hooks 214 to surrounding tissue.

Because the hooks 214 are integrally formed with the ring 200, the ring cannot be fomed merely by segmenting a tubular piece of ring material, and manufacture of the hooked ring is somewhat more difficult than manufacture of the ring embodiments described above. A ring 200 having integrally formed hooks 214 may be formed by molding a bioabsorbable or biodegradable material, such as polyglycolic acid. To prevent the ring material from sticking in the mold, a release agent is used to coat the mold. The release agent is selected for biocompatibility so that any release agent adhering to the ring will not induce adverse reactions.

The sutureless tethering ring 200 is disposed around one severed blood vessel end portion 212a with its hooked face 220 outward relative to the blood vessel end portion 212a as seen in FIG. 14 so that the blood vessel end portion extends entirely through its central opening 230. With forceps, the surgeon drapes a portion of the severed blood vessel end portion 212a over one hook 214 so that the hook punctures the blood vessel wall from its exterior 232 to its intima 234. The surgeon then repeats the procedure hooking the blood vessel portion 212a at evenly spaced locations until the blood vessel portion 212a is tethered under tension over the hooked face 220 of the ring 200 exposing a broad region of its intima 234. Next, the surgeon grasps a portion of the end of another severed blood vessel portion 212b and draws it over one hook 214 so that the hook punctures the blood vessel portion from its intima to its exterior 232. The procedure is repeated hooking the other blood vessel portion 212b at evenly spaced locations, tethering the blood vessel portion under tensions to the hooks 214 and bringing a broad portion of the intima of the blood vessel portion 212b into apposed contact with the intima 234 of the blood vessel end portion 212a that was initially tethered to the ring 200, thereby completing the anastomosis. Similar hooks can also be placed in the triangular and quadrangular configurations shown in FIGS. 16A and 16B. These are shown in FIG. 16C.

Illustrated in FIGS. 16A and 16B are alternative embodiments of anastomosis devices, 270, 270' which instead of being ring shaped are configured as polygons with polygonal shaped central openings 272, 272'. The number of verticies 274' of the polygon correspond directly to the number of sutures that are to be used for tethering the connected blood vessel portions, and the sutures are tethered to the verticies of the polygon which represent the points most remote from the geometric center. Thus the embodiment of an anastomosis device 270 shown in FIG. 16A is configured as an isosceles triangle and is used for anastomosing blood vessel portions with three sutures while the device 270' in FIG. 16B is square and is used for anastomosing blood vessel portions with four sutures.

As a means for attaching the sutures, the vertices are machined to provide concave grooves 276 facing outward. Under certain circumstances, it is found that such grooves 276 provide better resistance to suture slipping during surgery than do notches at the ends of rings. Like in the circular embodiments, the locations where the sutures are attached lie along a circle of substantially greater radius than the unstretched radii of the openings of the blood vessel end portions.

An advantage of polygonal shaped devices 270, 270' over a ring shaped device is that the polygonal central openings of the devices correspond to the shape that the blood vessel ends assume when they are tethered under radial stress allowing an anastomosis device of minimum size to be used. A polygonal anastomosis device is selected according to the radii of the openings so that when stretched, the end edges of the tethered vessel portions extend to the sides of the polygonal shaped interior opening 272.

Although square and triangular devices 270, 270' are shown for tying three and four sutures respectively, polygonal devices having more vertices 274 for attaching additional sutures can be formed. However, the size advantage relative to a circular configuration diminishes as the number of vertices increase. Also these shaped devices can be used for the sutureless technigue by adding thereto the additional hooks 214 as shown in FIG. 15.

In accordance with another aspect of the invention, an anastomosis ring 300 is prepositioned within a clamping device 301 such as that shown in FIG. 17, which holds the severed blood vessel portions 12a, 12b in close proximity to each other. The clamping device 301 provides a pair of clamps 302, one for holding each of the blood vessel portions 12a, 12b to be joined and base assembly 304 which carries the clamps 302 spaced apart a predetermined longitudinal distance 300. The anastomosis ring 300 is preferably integrally formed with a member or bar 306 of the base assembly 304, connected thereto by a frangible web 308 allowing the ring 300 to be easily detached from the base bar 306 after anastomosis.

In accordance with a still further aspect of the invention, the clamping device, indicated generally at 301, for use with an anastomosis ring 300 has clamps 302 which are pneumatically actuated to grip the blood vessel portions 12a, 12b with a suturing force that is a function of fluid or air pressure supplied to the clamps 302.

In the embodiment of the ring 300 and attached clamping device 301 illustrated in FIG. 16, a base bar 306 is generally in the shape of a triangular prism, and the anastomosis ring 300 is similar to the ring shown in FIG. 13 or in FIGS. 16A, or 16B. The base bar 306 and ring 300 as well as the frangible connecting web 308 extending between the base bar and the ring are integrally formed of bioabsorbable or biodegradable material, although only the ring is intended to be implanted in the body. The relative simplicity of the base bar 306 and ring 300 permit them to be formed by molding followed by some minor machining of the molded device.

As a means to adjust the axial or longitudinal spacing between the clamps 302 according to surgical requirements, the clamps are not directly joined to the base member but are carried by a pair of end caps or housings 310 which are interfitted to the base bar 306 and are slidable relative thereto. Thus, each housing 310 may be slid along the stationary bar 306 to adjust the spacing between housings.

The pneumatically or hydraulically operated clamps 302, which each extend from a front wall 316 of the end caps 310, are in this instance of the illustrated embodiment of the invention generally U-shaped in order to hold or grip the blood vessel portions 12a. The shape of each clamp 302 is defined by a rigid hollow tube 314 with a U-shaped cradle portion 315 extending from the front wall 316 of the end cap 310. The hollow tube 314 extends through the end cap 310 above the base bar 306, and a portion 320 extends outward from the rear wall 314 of the end cap 310 providing a port means for connection to flexible tubing 322 through which a pressurized fluid, such as air, is introduced from a source 324. Extending forward of the end cap 310 surrounding the cradle portion 315 of each hollow tube 314 is an elongated inflatable hollow, flexible tube or bladder 330 to which fluid is introduced via an open end 332 of the hollow tube 314. The degree of inflation of each bladder 330 determines the size of the cradle 336 and thereby the force of the clamp 302 on the blood vessel portion 12. By connecting flexible tubing 322 from the rearward portion 320 of the hollow tube 314 to a conduit 322 from the pressurized fluid source 324 having a control valve 342, the gripping force of the clamp 302 is very precisely predetermined and typically adjusted to provide between about 15 and about 25 gm. of force. With such precise adjustment, a firm grip can be assured without danger of microclamp damage to the blood vessel portions.

During surgery, the blood vessel portions 12a, 12b to be joined are loosely positioned in the cradles 336 of the clamps 302 providing sufficient blood vessel lengths inward of the clamps to bring their ends into close proximity. Then the bladders 330 are inflated by opening the valve 342 from the pressurized fluid source 324 to the degree necessary to provide the pressure corresponding to the desired gripping force of the clamps. With the blood vessel portions 12a,b clamped and the anastomosis ring 300 positioned in axial alignment with the clamp cradles 336, anastomosis is effected as described above, and upon completion, the bladders 330 are depressurized releasing the grip of the clamps from the anastomosed blood vessel. The web 308 is broken, and the clamping device 301 is removed.

The clamping device 301 is prepackaged with the attached ring 300 in a sterile manner, and upon opening the package (not shown), the device is immediately ready for use except perhaps for a quickly effected clamp spacing adjustment. The simple design of the clamping device 301 allows it to be manufactured relatively cheaply, an important consideration as it is intended that the entire clamping device be disposed subsequent to use.

Illustrated in FIGS. 18 and 19 is another embodiment of a pneumatically or hydraulically actuated clamping device, indicated generally at 401, which provides for precise determination of clamping force and which may be preattached for sterile packaging to an anastomosis ring 400. A base bar 402 is shaped as a rectangular bar on which is slidably mounted a pair of box-like hollow housings or chambers 403 each having a top 404, bottom 405, front 406, back 407 and a hollow rectangular interior region 408. Within the interior region 408 a pair of clamps 420 is placed. The base bar 402 is sized to fit snugly and intimately in slots 412 in the housing 403 and friction will hold the housing in adjusted positions on the base bar.

The slidable clamps 420 each include a bottom segment 422, an upwardly extending front flange 424, and an upwardly extending rear flange 426. The clamps 420 are interfitted to the chambers 403 with their bottom flanges 422 located over the base bar 402 with the rear flange 426 fully within the interior region 408. A blood vessel holding cradle 431 is defined between the chamber's front wall 406 and the front flange 424 of each clamp 420.

As a means to slide the clamps 420 rearward within the chamber 403, an elongated inflatable tube or bladder 432 is placed between the front wall 406 of the housing 403 and the upward rear flange 426. When pressurized with fluid or air, the bladder expands in size and acts to move the upward rear flange 426 and sliding the clamps 420 rearward and reducing the distance between the front side wall 406 of the chambers and the front cradle flange 424. The bladder 432 is pressurized from a source 471 through a conduit 433 extending through an aperture 413 in the rear wall 407 and rear flange 426 of the clamps 420. A valve 473 in the fluid or air conduit 433 is adjustable to inflate bladder 432 to the degree necessary to obtain the desired clamping force.

The anastomosis ring 400 extends forwardly from the base bar 402 and is connected thereto by a frangible web 434 which holds the prepositioned ring 400 in alignment with the vessels being clamped or gripped in the respective cradles.

Clamping is preformed by positioning the blood vessel 12, in the cradles and pressurizing the bladder 432 to effect clamping. The clamped vessel positions 12 are anastomosed by use of the prepositioned ring 400, and then the clamping pressure is released and frangible web 434 broken to release the anastomosed blood vessel. After surgery this simplistic clamping device can be disposed.

The clamping or gripping members are preferably formed of soft plastic tubing which provides a softer and more forgiving clamping or gripping pressure than the metal clamps heretofore used. With the pneumatic pressure and these softer materials the pressure and force application to the blood vessels are such as should reduce damage to the latter.

The anastomosis members and their surfgical uses will now be described in greater detail by way of specific example.

EXAMPLE I

Conventional and external ring technique anastomoses were performed on the superficial epigastric arteries on alternate sides of each of thirty male Sprague-Dawley strain rats weighing between 200 and 250 grams. Group 1 consisted of twenty external ring technique and twenty conventional technique anastomoses that were explored at one week, and again at four to six weeks. Group 2 consisted of ten external ring technique and ten conventional technique anastomoses that were left undisturbed until exploration at six weeks.

The rats were anesthetized with intraperitoneal pentobarbital, and the superficial epigastric artery was exposed through a transverse inguinal incision. External vessel diameters were 0.3 to 0.5 mm., measured prior to arterial isolation to avoid diameter variation induced by spasm or dilation due to smooth muscle relaxation by topical lidocaine. It was observed that an artery measuring 0.4 mm. in its undisturbed state could vary from 0.2 to 0.6 mm., from maximum vasoconstriction to maximum relaxation.

Three sutures 14 were used for the external ring technique, four to six sutures were used for the conventional anastomoses, dependent upon vessel diameter. Monofilament 100 nylon (Ethilon, Ethicon, tapir point BV75 needle) was used for all anastomoses, and the operations were performed at 25× to 50× magnification. The pattern of arterial pulsation was observed, and a radical patency test was performed thirty minutes after completion of each anastomosis to confirm initial patency.

Figure 3:
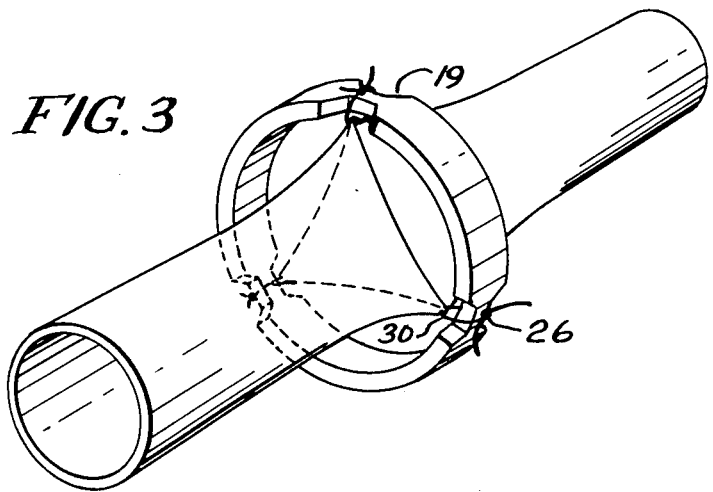
FIG. 3 is a perspective view of the ring of FIG. 1 with the sutures tethered to the ring.

The anastomosis rings 10 comprised 1 mm lengths of 18 gauge polytetrafluorethylene tubing having pairs of trapezoidal notches 19 formed at three locations 120° apart. For the external ring technique, the blood vessel 12 was placed in an adjustable double microclamp and transected. The loose adventitia was resected and the vessel ends irrigated with heparinized saline solution. Prevention of spasm was aided by the external application of 1% lidocaine. The ring 10 was slipped over one vessel end 12a, and three interrupted sutures 14 were placed through the full thickness of the vessel wall at 120° intervals, leaving the suture ends 32 untied. The vessel ends 12a,b were approximated by tying a surgeon's knot 20, and a free end 32 of all three sutures 14 were passed underneath the ring (FIG. 3). The ring 10 was centered over the anastomosis site, and each of the sutures 14 were tied around the ring 10 at the location of the preformed notches 19 (FIG. 4). In cross section, the vessel 12 then assumed a triangular pattern at the anastomosis site, with the natural elastic forces aiding tight apposition of the edges of the vessel intima between the three sutures 14. Distal release of the double microvascular clamp allowed retrograde flow, followed by proximal release and restoration of anterograde pulsatile flow.

Figure 5:
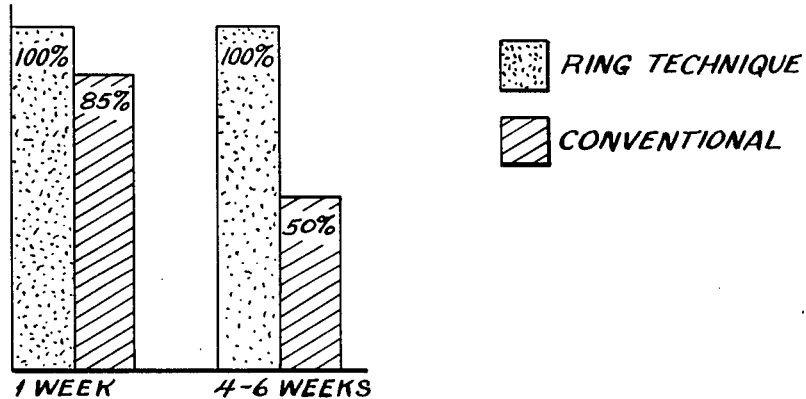
FIG. 5 is a bar graph representing patency of rat blood vessels sutured using the ring of the present invention as compared with suturing by conventional techniques.

In Group 1, all twenty external ring technique arterial anastomoses were patent both at one week and at four to six weeks. However, three of the twenty conventional anastomoses were thrombosed at one week, and an additional seven were thrombosed at four to six weeks (FIG. 5). Even among the originally patent, in seventeen of the twenty conventional anastomoses, diminished flow during radical patency testing was observed as compared to flow through anastomoses effected with the external ring technique. This may have been a factor in the cases of later thrombosis. The difference bewteen the 50% late patency rate by the conventional technique and the 100% patency rate by the external ring technique was statistically significant (p 0.01).

In Group 2, all ten external ring technique arterial anastomoses were patent at six weeks. In contrast, at six weeks, three of the ten conventional anastomoses were thrombosed and two others demonstrated diminished flow during radical patency testing. The difference between the 70% patency rate by the conventional technique and the 100% rate by the external ring technique again was statistically significant (P 0.02). In neither group was there any occurrence of aneurysms, hematomas, or wound infections.

Figure 6:
FIG. 6 is electron micrograph of a rat's blood vessel which has been severed and rejoined by the method and apparatus of the present invention.

FIG. 6 is a scanning electron micrograph portraying one of the patent rat anastomosis performed by the external ring technique with normal intimal healing. It will be noted that slight tipping of the ring occurred; however, in no case did such tipping impede blood flow.

EXAMPLE II

Rat inferior epigastric veins (generally 0.7 mm. in diameter) were anastomosed end-to-side to femoral veins (generally 1.5 mm. in diameter) by conventional techniques in twenty control rats, using 6–8 sutures per anastomosis, and in an experimental group of twenty rats by the external ring technique using rings 1 mm. long of 18 gauge polytetrafluorethylene with four notch pairs spaced 90° apart. The surgical technique was substantially identical to that used in Example I, except that the femoral veins were prepared for anastomosis by cutting 6 mm. openings in their side walls.

After five days, the control group had a 65% success rate whereas the experimental group exhibited 100% patency (P 0.01).

Figure 10:
FIG. 10 is a photo micrograph of an end-to-side rat blood vessel anastomosis.

FIG. 10 is a photo micrograph portraying one of the patent rat end-to-side anastomosis performed by the external ring technique with normal intimal healing.

The external ring technique provides a direct approach to overcome the vessel's inherent circumferential compressive stress, provide maximal radial tethering forces at the site of anastomosis, and actually dilates the vessel at the very location platelet aggregation occurs in the early post-operative phase. These important factors explain the increased success rate in the difficult model of the 0.4 mm. size inferior epigastric artery of the rat. With any constant level of surgical skill, the success rate of microvascular repair falls as the vessel size decreases. Of course, the degree of skill acquired by the surgeon is an important factor in the success rate of microvasuclar repair, and the use of the external ring technique may actually improve any given level of surgical skill.

The external ring provided by the application is simply formed and easy to use. In surgery, where several anastomoses need be performed, the external ring technique will substantially reduce the time of the operation. The multidirectional radial tethering helps to assure dilation of the passageway at the interconnection, and interconnection with a large blood passageway is generally assured. The technique draws the intima of the severed ends in tight apposition to each other providing a fluid-tight interconnection and exposure of blood substantially entirely with the intima, reducing the chance of significant post operative thrombosis.

The use of pneumatically actuated and adjustable clamping devices, as described with reference to the above embodiments, permits vascular surgery with substantially no microclamp damage to blood vessels. Prepositioning of the anastomosis device within the clamping device can be expected to significantly shorten surgery, particularly where a large number of blood vessels need to be joined.

While the invention has been described in terms of a preferred embodiment, modifications obvious to one with ordinary skill in the art may be made without departing from the scope of the invention. The embodiment of the external ring, described herein, is simple; however, modifications in ring design will be made depending upon the material used and surgical considerations. Although the invention has been described in terms of a fully encircling member or ring, an incomplete, but substantially encircling ring member might be used instead allowing it to be slipped around the blood vessel after sutures have interconnected the blood vessel ends, and the tethering forces in the several radial directions could be relied upon to hold such an incomplete ring in place around the blood vessel.

Various features of the invention are set forth in the following claims.

What is claimed is:

1. Apparatus for anatomosing a first living vessel of an external diameter having a prepared end and an open first passageway therein to a second living vessel having a second passageway and a prepared opening, the apparatus comprising a substantially encircling anastomosis member of biocompatible material, at least three suture holding means attached to said encircling member in a detachable manner at each of three circumferentially spaced connecting locations, a suture held by each of said suture holding means, and a needle pre-attached to each of said sutures, whereby said encircling member may be prepackaged in a sterile manner along with said pre-attached sutures and needles positioned at said connecting locations and whereby said pre-attached sutures and needles are used during surgery to join the end of the first vessel and the second vessel to said encircling member at said connecting locations with the end of the first living vessel stretched radially outward to tend the same and to assist in holding the end of the first vessel in sealing apposition against the second vessel, said encircling member being sufficiently rigid to maintain its shape while serving as the sole support of said joined vessels connected thereto.

2. Apparatus in accordance with claim 1 wherein said encircling member is formed of a biodegradable material.

3. Apparatus according to claim 1 wherein each of said sutures has a pre-formed loop at the end opposite said pre-attached needle.

4. A device for holding a pair of living vessel portions for anastomosis comprising
an elongated base,
a pair of rigid, hollow tubular members extending from said base, each having a generally U-shaped configuration and having an opening,
a pair of elongated tubular bladders, each of which encircles one of said rigid members, generally following the U-shaped contour thereof, and
fluid pressure means communicating with said bladders through said openings of said hollow tubes for inflating said bladders, whereby said inflated bladders exert a gripping force on vessel portions cradled therein that is proportional to the fluid pressure supplied to said bladders by said fluid pressure means.

5. A device according to claim 4 including means for positioning said rigid members with said encircling bladders axially relative to each other.

6. Apparatus for anastomosing a first living vessel to a second living vessel each having open ends comprising in a combination
an elongated base,
a pair of clamping means extending from said base at spaced apart locations for clamping the living vessel ends in axial alignment,
means associated with said base for adjusting the relative axial spacing of said clamping means,
a unitary member formed of biocompatible material having a central opening and being adapted for joining said vessels with their open ends in sealed communication with each other, said unitary member being sufficiently rigid to maintain its shape while serving as the sole support of the joined vessel ends, and
means connected to said base between said clamping means for detachably supporting said unitary member in axial alignment with said pair of clamping means,
whereby said first and second vessels may be clamped in said axially aligned clamping means, said clamped vessels approximated by adjusting the axial spacing of said clamping means, said vessel ends attached to said rigid unitary member in sealed communication with each other, said vessels released from said clamping means and said unitary member detached from said supporting means.

7. Apparatus according to claim 6 wherein said supporting means is a frangible support securing said unitary member to said base.

8. Apparatus according to claim 6 wherein said clamping means includes inflatable bladder means for receiving pressurized fluid and means for supplying a predetermined fluid pressure to said bladder to provide a predetermined gripping force of said clamping means on said vessels.

9. A device according to claim 8 wherein each of said clamping means comprises a rigid member having a generally U-shaped configuration and an inflatable bladder surrounding said rigid member and communicating with said fluid pressure supplying means.

10. A device according to claim 8 wherein said rigid member is a hollow tube having an opening, and said bladder communicates with said fluid pressure supplying means through said opening of said hollow tube.

11. A device according to claim 8, each of said clamping means comprising a first cradle side and a slide member carrying an opposed second cradle side, said bladder means being positioned to move said slide member and position said second cradle side relative to said first cradle side according to the fluid pressure supplied thereto.

12. A device according to claim 8 wherein said fluid pressure supplying means is adapted to inflate said bladder means so that said clamping means grip said vessels with forces of between about 15 and 25 grams.

* * * * *

UNITED STATES PATENT AND TRADEMARK OFFICE
CERTIFICATE OF CORRECTION

PATENT NO. : 4,624,255

DATED : November 25, 1986

INVENTOR(S) : Robert R. Schenck and Harry P. Weinrib

It is certified that error appears in the above-identified patent and that said Letters Patent is hereby corrected as shown below:

Column 3, Line 10, change "anastpmosis" to --anastomosis--;

Column 12, Line 65, change "tend" to --tent--;

Column 13, Line 32, after "in" delete "a".

Signed and Sealed this

First Day of December, 1987

Attest:

DONALD J. QUIGG

Attesting Officer      Commissioner of Patents and Trademarks